US009164061B2

(12) United States Patent
Thegel et al.

(10) Patent No.: US 9,164,061 B2
(45) Date of Patent: Oct. 20, 2015

(54) ARRANGEMENT FOR CRACK DETECTION IN METALLIC MATERIALS IN A METAL MAKING PROCESS

(71) Applicant: ABB Technology AG, Zurich (CH)

(72) Inventors: Lennart Thegel, Vasteras (SE); Sten Linder, Trosa (SE)

(73) Assignee: ABB Technology AG (CH)

( * ) Notice: Subject to any disclaimer, the term of this patent is extended or adjusted under 35 U.S.C. 154(b) by 0 days.

(21) Appl. No.: 14/202,988

(22) Filed: Mar. 10, 2014

(65) Prior Publication Data

US 2014/0197825 A1 Jul. 17, 2014

Related U.S. Application Data

(63) Continuation of application No. PCT/EP2012/069065, filed on Sep. 27, 2012.

(30) Foreign Application Priority Data

Sep. 29, 2011 (EP) ..................................... 11183353

(51) Int. Cl.
*G01N 27/82* (2006.01)
*B21B 38/00* (2006.01)
(Continued)

(52) U.S. Cl.
CPC ................ G01N 27/82 (2013.01); B21B 38/00 (2013.01); G01N 27/9026 (2013.01); *G01L 3/105* (2013.01); *G01R 33/18* (2013.01)

(58) Field of Classification Search
CPC ....... G01L 3/105; G01L 3/101; G01L 9/0004; G01L 1/125; G01L 1/127; G01L 3/102; G01R 33/18; G01N 27/82

USPC .................................... 324/209, 210; 73/148
See application file for complete search history.

(56) References Cited

U.S. PATENT DOCUMENTS 4,584,746 A * 4/1986 Tivolle et al. ................. 29/81.08
4,746,858 A * 5/1988 Metala et al. ................. 324/200
(Continued)

FOREIGN PATENT DOCUMENTS

| EP | 1033571 A2 | 9/2000 |
| EP | 1033571 B1 * | 7/2006 |
| GB | 2401947 A | 11/2004 |

OTHER PUBLICATIONS

Translation of EP 1033571.*

(Continued)

*Primary Examiner* — Jermele M Hollington
*Assistant Examiner* — Christopher McAndrew
(74) *Attorney, Agent, or Firm* — Whitmyer IP Group LLC

(57) ABSTRACT

An arrangement for a metal making process for detecting cracks along a strip of a metallic material moving in relation to the arrangement. The arrangement includes a coil arrangement fixedly arranged during crack inspection, having: a first winding portion extending in a first direction for inducing a first current in the first direction; a second winding portion extending in a second direction for inducing a second current in the second direction, the first direction and the second direction intersecting each other; a first receiver coil arranged to detect a magnetic field generated by the first current; and a second receiver coil arranged to detect a magnetic field generated by the second current, the magnetic field generated by the first current and the magnetic field generated by the second current providing a measure of whether a crack is present in the portion of the strip.

25 Claims, 8 Drawing Sheets

(51) Int. Cl.
   *G01N 27/90* (2006.01)
   *G01R 33/18* (2006.01)
   *G01L 3/10* (2006.01)

(56) References Cited

U.S. PATENT DOCUMENTS

| | | | |
|---|---|---|---|
| 5,015,951 A * | 5/1991 | Melcher | 324/232 |
| 5,453,689 A * | 9/1995 | Goldfine et al. | 324/239 |
| 5,617,024 A * | 4/1997 | Simpson et al. | 324/209 |
| 5,648,721 A * | 7/1997 | Wincheski et al. | 324/240 |
| 5,698,977 A * | 12/1997 | Simpson et al. | 324/209 |
| 5,793,206 A * | 8/1998 | Goldfine et al. | 324/242 |
| 6,188,218 B1 * | 2/2001 | Goldfine et al. | 324/243 |
| 6,377,040 B1 * | 4/2002 | Hell | 324/240 |
| 7,026,811 B2 * | 4/2006 | Roney et al. | 324/242 |
| 2004/0004475 A1 | 1/2004 | Goldfine et al. | |
| 2010/0079157 A1 * | 4/2010 | Wincheski et al. | 324/699 |

OTHER PUBLICATIONS

International Preliminary Report o Patentabiity Application No. PCT/EP2012/069065 Completed: Dec. 11, 2013 20 pages.

International Search Report and Written Opinion of the International Searching Authority Application No. PCT/EP2012/069065 Completed: Dec. 19, 2012; Mailing Date: Jan. 3, 2013 12 pages.

* cited by examiner

ARRANGEMENT FOR CRACK DETECTION IN METALLIC MATERIALS IN A METAL MAKING PROCESS

FIELD OF THE INVENTION

The present disclosure generally relates to quality inspection of a metallic material, and in particular to crack detection in the surface of the metallic material by means of induction in a metal making process.

BACKGROUND OF THE INVENTION

It is known to detect cracks in metallic materials for instance in steel production. Inductive techniques have for instance been used for this purpose. When using an inductive technique a current is induced in the metallic material, e.g. a slab or a metal sheet, by means of a time-varying magnetic field generated by a transmitter coil fed with a likewise time-varying current. When the induced current encounters a crack in the metallic material, the crack constitutes an obstacle to the induced current. As a result, the crack alters the induced current at the crack as compared to a metallic material without a crack. The altered current provides a change in the magnetic field around the current. The change in the magnetic field is measured by a receiver coil, whereby it can be determined that a crack is present in the inspected surface portion of the metallic material.

When using inductive techniques for crack detection in metallic materials, the surface of the metallic material is typically searched by means of coils being moved across that portion of the surface which is to be inspected. GB 2 401 947 discloses an apparatus and for inspection of critical surfaces on aircraft engine disks. One embodiment disclosed in GB 2 401 947 is depicted in FIG. 5. This embodiment comprises a transmitter coil 38 that is in the form of a right-angled triangle. Receiver coils 32-1 and 32-2 are arranged along respective adjacent sides 38-1 and 38-2 of the right angle of the triangular transmitter coil 38. The sides 38-1 and 38-2 of the triangle induce orthogonal currents in metallic material that is being inspected for cracks. Thereby cracks having different orientation may be detected by the receiver coils 32-1 and 32-2. Crack inspection is conducted by moving the apparatus along the surface of the aircraft engine disk.

EP 1 033 571 A2 discloses a probe which includes a first substrate in or on which a probe coil is arranged. A second probe coil at least partially overlaps the area covered by the first probe coil, as viewed from above. The second coil is arranged in or on a second substrate. A stack of further substrates may be provided for further probe coils. At least one of the substrates is a film substrate made of flexible material. The first and second coils are used for detecting cracks or faults with mutually differing orientation in the component being tested. A photolithographic method of manufacture is also claimed.

U.S. Pat. No. 4,584,746 discloses a device for detecting cracks in steel slabs leaving continuous casting. The devices comprises two crack detecting units placed on either side of the passage of a slab leaving continuous casting and two descaling and cooling units located upstream of the detection units. Each detection unit comprises a mobile frame and a bead which slides vertically with respect to the frame and which bears one vertical sensor and three horizontal sensors. The sensors are induction coils placed in a container which is surrounded by a forwardly open metal casing. One application of the device is the automatic switching of defective slabs towards a reprocessing unit.

In production processes of metallic products it has proved to be difficult to utilise equipment of the above-mentioned type. Firstly such crack inspections may take too long time for fitting into a production flow. Secondly the mechanical devices required for inspection become too expensive and too sensitive for the conditions, e.g. high temperatures in a continuous casting process, which often prevail during production.

SUMMARY OF THE INVENTION

It would be advantageous to be able to provide a crack detection arrangement for a metal making process, which is fixedly arranged during crack inspection, especially for crack detection on surfaces of hot metal in metal casting such as continuous casting processes. Such an arrangement would be more robust than a moving arrangement in the harsh environment of metal making of the above-mentioned type. Moreover, by properly designing a crack detection arrangement that is fixed during crack inspection, crack inspection could be carried out more rapidly than with existing solutions. In metal making, the distance between the metallic material to be inspected and the sensors of an inductive crack detector arrangement will inevitably be in the range of about 10-20 mm. This is firstly because the sensors of the crack detection arrangement must be shielded by means of a protection member, such as a disk, from dirt and possibly from heat if the surface of the metallic material is hot. In the latter case cooling of the protection member/sensors may be necessary e.g. by means of water, as metallic material in metal making may have surface temperatures of up to 1000 degrees Celsius, or even higher. Cooling arrangements are advantageously provided between the sensors of the crack detection arrangement and the surface of the metallic material that is to be inspected. Secondly the sensors and protection member/cooling system should be further distanced from the measurement surface of the metallic material because the surface of the metallic material may be curved and/or irregular; by sufficiently distancing the sensors from the surface to be inspected, the risk of mechanical damage of the sensors, protection member and cooling system is reduced.

Existing inductive sensing solutions, such as the one described in GB 2 401 947, are not suitable for usage in a metal making process, especially for inspection of hot metal surfaces. The reasons are that the dimension of the transmitter coil and the distance between the transmitter coils and receiver coil of GB 2 401 947 prevents the device from inducing a current with a sufficient magnitude in a metallic material in a metal making process, where the distance between the coil arrangement and the surface to be inspected should be in a range of about 10-20 mm. In GB 2401 947 receiver coils or sensing elements are mentioned to advantageously have a dimension of 1*1 mm or smaller for increased resolution, which indicates that crack measurements must be made at essentially the same distance. Further details regarding these conclusions will be provided in the detailed description. As an example of the effect of the distance between the surface to be inspected and the transmitter coil, only about 10-20% of the magnetic field generated by the transmitter coil interacts with the metallic material if the transmitter coil is arranged at a distance of 20 mm and the length/width dimension of the transmitter coil is 10 mm. Hence, the sensitivity for crack detection in metallic material in a metal making process is greatly reduced.

In view of the above, a general object of the present disclosure is to provide inductive crack detection over large areas of metallic material in a metal production flow.

Another object of the present disclosure is to reduce the mechanical wear subjecting an arrangement for crack detection during crack inspection.

Yet another object of the present disclosure is to provide inductive crack detection without moving part usable for large work pieces such as slabs, plates and strips, thus increasing reliability and decreasing costs of such detection.

Thus, according to a first aspect of the present disclosure there is provided an arrangement for a metal making process for detecting cracks along a strip of a metallic material moving in relation to the arrangement, the arrangement comprising: a coil arrangement which is fixedly arranged during crack inspection, which coil arrangement has a first winding portion extending in a first direction for inducing a first current in the first direction in a portion of the strip; a second winding portion extending in a second direction for inducing a second current in the second direction in the portion of the strip, the first direction and the second direction intersecting each other; a first receiver coil arranged to detect a magnetic field generated by the first current; and a second receiver coil arranged to detect a magnetic field generated by the second current, the magnetic field generated by the first current and the magnetic field generated by the second current providing a measure of whether a crack is present in the portion of the strip and a direction of the crack.

By means of the present disclosure, contactless inspection of cracks over large areas of metallic material may be carried out. Moreover, due to the first winding portion and the second winding portion being arranged such that their directions of extensions intersect, cracks having different orientation may be detected and the direction in which the crack mainly extends may be determined also with a coil arrangement that is fixedly arranged during crack inspection. Thereby the arrangement will be mechanically much more simple than solutions according to prior art, hence resulting in lower costs, more reliable operation and a longer lifetime.

In one embodiment the first direction and the second direction are essentially perpendicular. Thereby optimal crack detection with respect to cracks having different orientation may be provided.

In one embodiment the second winding portion is arranged downstream of the first winding portion with respect to a direction of movement of a metallic material during crack inspection thereof. Hence one crack may be inspected by both the first winding portion, detecting cracks in mainly a first direction, and by the second winding portion which is arranged to detect cracks mainly in a second direction essentially orthogonal to the first direction, whereby the direction in which a crack extends may be determined.

In one embodiment the first receiver coil is arranged at a side of the first winding portion and the second receiver coil is arranged at a side of the second winding portion, the first receiver coil and the second receiver coil both being arranged in the same plane as the first winding portion and the second winding portion. By means of this arrangement the magnetic fields caused by the induced first current and second current in the metallic material may efficiently be detected by the receiver coils.

In one embodiment a winding of the first receiver coil is arranged in parallel with the first winding portion and a winding of the second receiver coil is arranged in parallel with the second winding portion. Hence, an optimal orientation of the first receiver coil and the second receiver coil are obtained for detecting the magnetic fields in the metallic material.

In one embodiment the first winding portion has an essentially constant direction of extension along a distance where the first winding portion is parallel with the winding of the first receiver coil, and the second winding portion has an essentially constant direction of extension along a distance where the second winding portion is parallel with the winding of the second receiver coil. Hence the currents induced in the metallic material will have an essentially constant direction of propagation over a distance corresponding to a strip width which is desired to be measured for cracks.

One embodiment comprises a signal generator arranged to feed a time-varying current to the first winding portion and the second winding portion for inducing the first current and the second current in the metallic material.

In one embodiment the first winding portion defines a first leg of an essentially right angled triangular transmitter coil and the second winding portion defines a second leg of the essentially triangular transmitter coil, the first leg and the second leg being essentially perpendicular legs.

In one embodiment the first winding portion and the second winding portion form part of electrically separated coils, each of the first winding portion and the second winding portion being arranged to be fed with an individual time-varying current.

In one embodiment each of the first winding portion and the second winding portion form part of a respective rectangular shaped coil transmitter coil.

In one embodiment the time-varying current is a pulse train. Measurements by the first receiver coil and the second receiver coil may thereby advantageously be taken between subsequent pulses.

One embodiment comprises a control unit for controlling the signal generator to alternatingly provide the time-varying current to each of the first winding portion and the second winding portion to thereby alternatingly induce the first current and the second current in the metallic material.

One embodiment comprises a computing unit arranged to receive signals based on the magnetic field detected by the first receiver coil and on the magnetic field detected by the second receiver coil for determining whether a crack is present in the strip.

In one embodiment the computing unit is arranged to determine a direction of extension of a detected crack based on the magnetic field detected by the first receiver coil and on the magnetic field detected by the second receiver coil.

One embodiment comprises a third receiver coil having a winding arranged along the same axis as the first receiver coil, the winding of the third receiver coil being arranged to detect the magnetic field generated by the first current.

One embodiment has a third winding portion parallel with the second winding portion for inducing a third current in the metallic material, and a fourth receiver coil having a winding arranged in parallel with the winding of the second receiver coil, the winding of the fourth receiver coil being arranged to detect a magnetic field generated by the third current in the metallic material.

According to one embodiment the first winding portion forms part of a transmitter coil, which transmitter coil has a smallest dimension, in a plane parallel to a surface of a metallic material to be inspected for cracks when the surface is being inspected for cracks, which is at least twice as large as a distance from the first winding portion to said surface.

According to one embodiment the second winding portion forms part of a transmitter coil, which transmitter coil has a smallest dimension, in a plane parallel to a surface of a metallic material to be inspected for cracks when the surface is being inspected for cracks, which is at least twice as large as a distance from the second winding portion to said surface.

According to one embodiment the smallest dimension of the transmitter coil is at least three times as large as the distance from the first winding portion to the surface of the metallic material when the surface is being inspected for cracks.

According to one embodiment the smallest dimension of the transmitter coil is at least three times as large as the distance from the second winding portion to the surface of the metallic material when the surface is being inspected for cracks.

According to one embodiment the first winding portion is arranged at a first distance from the first receiver coil, and wherein the first winding portion is arranged at a second distance from a surface of a metallic material to be inspected for cracks when the metallic material is in position for crack inspection, wherein the first distance and the second distance differ less than 40%.

According to one embodiment the first distance and the second distance differ less than 20%.

According to one embodiment the second winding portion is arranged at a first distance from the second receiver coil, and wherein the second winding portion is arranged at a second distance from a surface of a metallic material to be inspected for cracks when the metallic material is in position for crack inspection, wherein the first distance and the second distance differ less than 40%.

According to one embodiment the first distance and the second distance differ less than 20%.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

The inventive concept will now be described, by way of example, with reference to the accompanying drawings, in which:

FIG. 1B shows how a metallic material is inspected for cracks by means of the arrangement in FIG. 1a;

FIG. 2B shows how a metallic material is inspected for cracks by means of the arrangement in FIG. 2a;

DETAILED DESCRIPTION OF THE INVENTION

The inventive concept will now be described more fully hereinafter with reference to the accompanying drawings, in which certain embodiments of the inventive concept are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art.

The arrangement presented herein is adapted to detect cracks in a metallic material. The arrangement may also be able to determine various parameters associated with a detected crack such as the orientation of the crack in the metallic material. Advantageously, the arrangement may be used under extreme conditions, for instance in a metal making process such as a casting process or a rolling process.

Any metallic material which has a conductivity which is high enough to allow a current to be induced in the metallic material may be inspected by means of the arrangements presented herein.

Figure 1A:
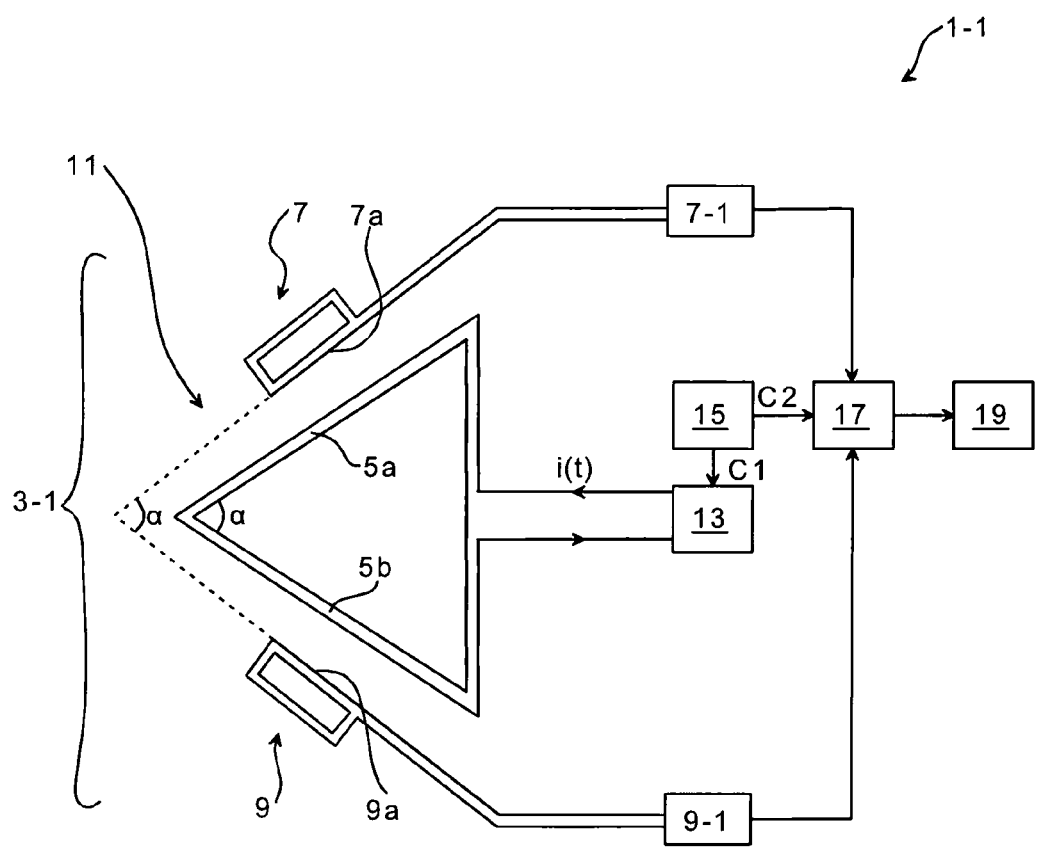
FIG. 1A is a schematic top view of a first example of an arrangement for crack detection in a metallic material.

FIG. 1a shows a schematic view of a first example of an arrangement for detecting cracks along a strip in a moving metallic material. Arrangement 1-1 comprises a coil arrangement 3-1, a first amplifying circuit 7-1, a second amplifying circuit 9-1, a signal generator 13, a control unit 15, a signal processing unit 17, and a computing unit 19.

The coil arrangement 3-1 comprises a transmitter coil in the form of an essentially right angled triangular transmitter coil 11 having a first winding portion 5a defining a first leg of the essentially right angled triangular transmitter coil 11, and a second winding portion 5b defining a second leg of the essentially right angled triangular transmitter coil 11. In one embodiment the first leg and the second leg have an angle α between them, the angle α being essentially 90 degrees. Thus, the first winding portion 5a and the second winding portion 5b may be essentially perpendicular. To this end, the first winding portion 5a and the second winding portion 5b define adjacent legs of the essentially right angled triangular transmitter coil 11. The first winding portion 5a and the second winding portion 5b are hence electrically connected and arranged to receive and conduct the same time-varying current i(t) from the signal generator 13.

In one embodiment the transmitter coil may be a triangular transmitter coil in the form of an isosceles triangle or an essentially isosceles triangle. In such an embodiment the first winding portion is provided at one of the isosceles sides defining the first leg of the triangular transmitter coil and a second winding portion is provided at the other isosceles side defining a second leg of the triangular transmitter coil. The angle between the two isosceles sides may in one embodiment be essentially 90 degrees.

In some embodiments of the triangular transmitter coil or the essentially right angled triangular transmitter coil, the angle α between the first leg and the second leg may be anywhere in the range 0<α<180°, i.e. the angle may be greater than zero degrees and less than 180 degrees.

The coil arrangement 3-1 further comprises a first receiver coil 7 having a winding portion 7a, and a second receiver coil 9 having a winding portion 9a. The first receiver coil 7 is arranged at a side of the first winding portion 5a and the second receiver coil 9 is arranged at a side of the second winding portion 5b. The first receiver coil 7 and the second receiver coil 9 are arranged at such a distance from the first winding portion 5a and the second winding portion 5b, respectively, that they are able to detect magnetic fields from induced currents created in a metallic material by the first winding portion 5a and the second winding portion 5b, respectively.

In one embodiment the first receiver coil 7 and the second receiver coil 9 are essentially rectangular coils, each having an interior centre point. The winding portion 7a defines a side of the essentially rectangular receiver coil 7. The winding portion 9a defines a side of the essentially rectangular receiver coil 9.

Figure 1B:
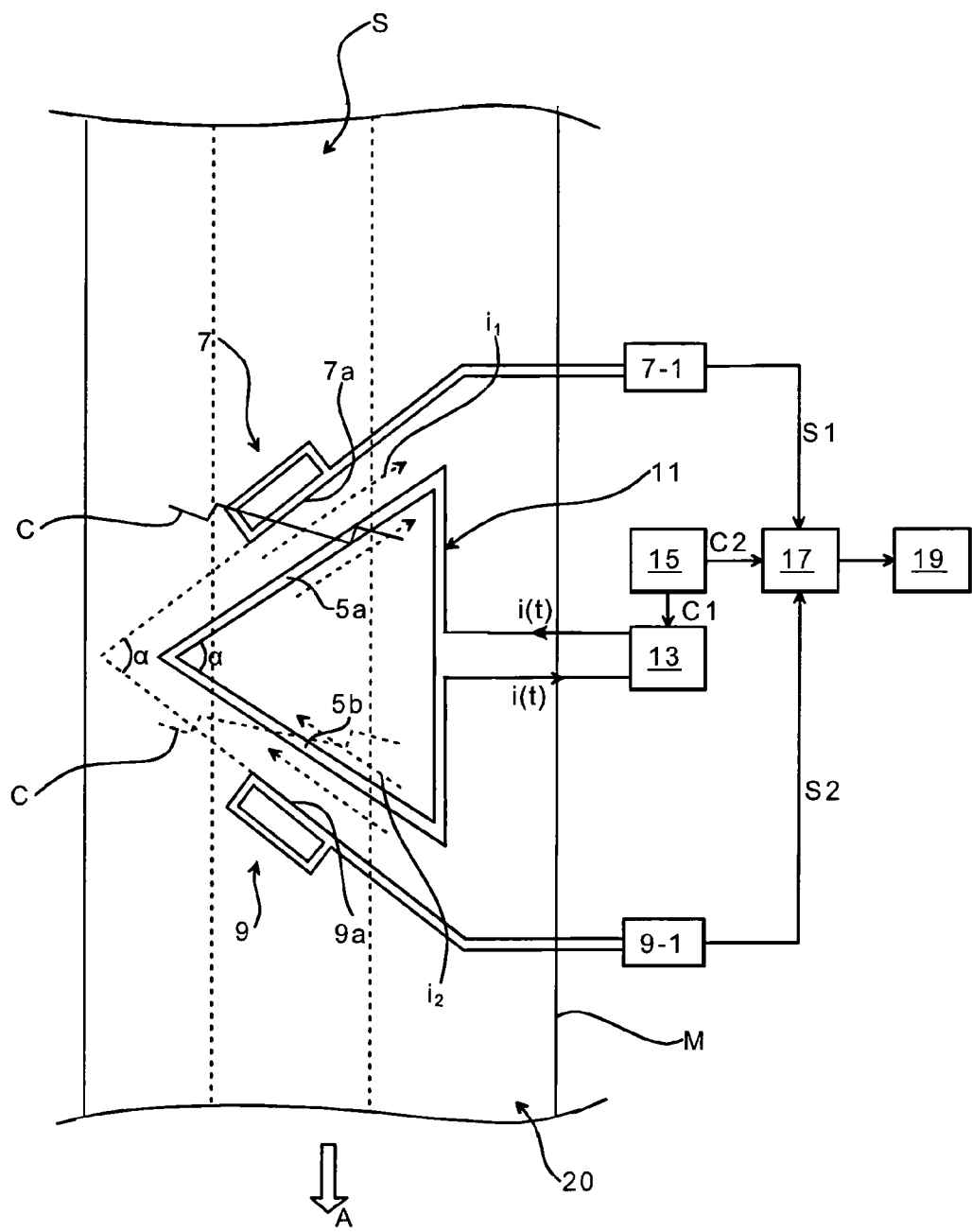

The interior centre point of the first receiver coil 7 may preferably be arranged at a distance from the first winding portion 5a corresponding to the distance at which the first winding portion 5a is located from a surface 21 of a metallic material M to be inspected for cracks, as shown in FIG. 1b. The interior centre point of the second receiver coil 9 may preferably be arranged at a distance from the second winding portion 5b corresponding to the distance at which the second winding portion 5b is located from the surface 21 of the metallic material M to be inspected for cracks. These relations may apply to any example disclosed herein, e.g. also for rectangular or essentially rectangular shaped transmitter coils. In one embodiment winding portion 7a of the first receiver coil 7 is arranged in parallel with the first winding portion 5a. Winding portion 9a of the second receiver coil 9 is arranged in parallel with the second winding portion 5b. Hereto, winding portion 7a of the first receiver coil 7 and winding portion 9a of the second winding portion 9 are essentially perpendicular to each other, having essentially the same angle α as the first winding portion 5a and the second winding portion 5b between them. It should be noted that the winding portions 7a and 9a may in variations of the first example be arranged in other ways relative the first winding portion 5a and the second winding portion 5b, respectively. To this end, the receiver coils may preferably be arranged adjacent their respective transmitter winding, i.e. first and second winding portions.

In one embodiment, winding portions 7a and 9a have longitudinal extensions corresponding to a width of the strip desired to be inspected for cracks.

In one variation of the arrangement 1-1, the first winding portion 5a, the second winding portion 5b, the first receiver coil 7 and the second receiver coil 9 are essentially flat coils, i.e. their dimension in a direction parallel with a normal to the surface of the metallic material when inspecting the metallic material for cracks by means of the arrangement 1-1 is several times less than any other dimension of the arrangement 1-1. In such a variation they have an essentially uniform height dimension, preferably being printed on or otherwise arranged on or in a substrate.

In one embodiment the essentially right angled triangular transmitter coil has a height extension which is several times less than its length extension or width.

The first winding portion 5a and the second winding portion 5b are arranged to receive a time-varying current i(t), from the signal generator 13. In one variation of the arrangement 1-1, the time-varying current may be a pulse train. The time-varying current may hence be a sudden change of current magnitude from one level to another, for instance from a constant current level to zero current. The signal generator 13 is arranged to receive instructions regarding the type of signal to generate, and when to generate it, via a control signal C1 provided by the control unit 15.

Turning now to FIG. 1b the arrangement 1-1 will now be described in operation.

The coil arrangement 3-1 is typically kept fixed during crack inspection of a metallic material. If the arrangement 1-1 is operated under extreme conditions, e.g. high temperatures, the coil arrangement 3-1 may be cooled for instance by means of a cooling fluid such as water. This applies to all examples disclosed herein.

During operation, the metallic material M which is to be inspected for cracks moves in a direction A relative the coil arrangement 3-1, preferably with an essentially constant speed, at one side of the coil arrangement 3-1. To this end, either coil arrangement 3-1 may be moved linearly with an essentially constant speed, or alternatively the metallic material M may be moved relative the coil arrangement 3-1. The metallic material M may for instance, relative the coil arrangement 3-1, move under the coil arrangement 3-1. Thus, the coil arrangement 3-1 can be positioned above a surface 20 of the metallic material M as it moves under the coil arrangement 3-1. Thereby, the coil arrangement 3-1 can be used to inspect a strip S along the surface 20 of the metallic material M. It is to be noted that the coil arrangement could of course also be positioned e.g. under the metallic material, thereby obtaining the same effect as if positioned above the metallic material.

For the purposes of crack inspection, and in particular for determining additional crack parameters such as crack direction, the second winding portion 5b is arranged downstream of the first winding portion 5a with respect to the direction of movement A of the metallic material M. The distance from the first winding portion 5a and the distance from the second winding portion 5b to the surface 20 of the metallic material M during crack inspection is considerably less than a distance from the base of the essentially right angled triangular transmitter coil to the vertex between the first leg and the second leg. In general, for all examples of transmitter coils presented herein the distance from the transmitter coil to the surface of the metallic material to be inspected for cracks is considerably less than the size of the transmitter coil in a plane parallel with the surface 20 when the metallic material M is in position for inspection.

In a first step during operation, the essentially right angled triangular transmitter coil 11 is fed with a time-varying current i(t) from the signal generator 13. The first winding portion 5a and the second winding portion 5b are hence both fed with the same time-varying current i(t).

As the time-varying current i(t) flows through the first winding portion 5a, a magnetic field is generated around the first winding portion 5a. When the metallic material M is arranged adjacent the first winding portion 5a the magnetic field generated around the first winding portion 5a induces a first current $i_1$ in a portion of the strip S of the metallic material M. The first current $i_1$ is essentially parallel with the flow direction of the time-varying current i(t) in the first winding portion 5a, the first current $i_1$ flowing in the opposite direction relative the flow direction of the time varying current i(t) in the first winding portion 5a. By means of the first current $i_1$ a magnetic field is generated around the first current $i_1$ in the metallic material M.

As the time-varying current i(t) flows through the second winding portion 5b, a magnetic field is generated around the second winding portion 5b. When the metallic material M is arranged adjacent the second winding portion 5b the magnetic field generated around the second winding portion 5b induces a second current $i_2$ in a portion of the strip S of the metallic material M.

The second current $i_2$ is essentially parallel with the flow direction of the time-varying current i(t) in the second winding portion 5b, the second current $i_s$ flowing in the opposite direction relative the flow direction of the time varying current i(t) in the second winding portion 5b. By means of the second current $i_2$ a magnetic field is generated around the second current $i_2$ in the metallic material M.

Due to the location of the first receiver coil 7, in relation to the first winding portion 5a, the magnetic field can be detected by the first receiver coil 7. Hereto, the magnetic field induces a voltage in the first receiver coil 7, which voltage is amplified in the first amplifying circuit 7-1. The amplified voltage in the following referred to as a first signal S1, is sent to the signal processing unit 17.

Due to the location of the second receiver coil 9, in relation to the second winding portion 5b, the magnetic field can be detected by the second receiver coil 9. Hereto, the magnetic field induces a voltage in the second receiver coil 9, which voltage is amplified in the second amplifying circuit 9-1. The amplified voltage, in the following referred to as a second signal S2, is sent to the signal processing unit 17.

Due to the movement of the metallic material M, the first current $i_1$ and the second current $i_2$ can be induced in the same portion of the metallic material M at different instances in time. To this end the magnetic field detected by the first receiver coil 7 and the magnetic field detected by the second receiver coil 9 provide a measure of whether a crack is present in the inspected portion of the strip and also information regarding e.g. the orientation of the crack, as will be described in more detail in the following.

Since the first winding portion 5a and the second winding portion 5b have different orientation, in this example being essentially perpendicular, and are thereby arranged to induce the first current $i_1$ and the second current $i_2$ in the metallic material M in a first direction and a second direction, respectively, the first direction and the second direction intersecting each other, cracks having different orientation may be detected by means of the first receiver coil 7 and the second receiver coil 9.

Cracks having a longitudinal extension perpendicular to the longitudinal extension of a winding portion 5a, 5b provide a greater change in the induced current associated with that winding portion 5a, 5b and thus a greater change of the induced voltage in the associated receiver coil 7, 9 compared to a crack having a longitudinal extension which is parallel with the longitudinal extension of a winding portion 5a, 5b. In other words, the essentially perpendicular flow directions of the first current $i_1$ and the second current $i_2$ result in that the first current $i_1$ and the second current $i_2$ encounter the same crack from different directions as the metallic material moves in the direction of movement. The first current $i_1$ and the second current $i_2$ are thereby altered differently, whereby the corresponding magnetic fields are altered differently. As can be seen in the example of FIG. 1b, the crack C first passes under the first receiver coil 7, thereby altering the strength of the magnetic field. Since the crack is transverse to the first winding portion 5a and thus the first current $i_1$ the magnetic field strength is noticeably altered. The change in the magnetic field strength is detected by the first receiver coil 7.

As the metallic material M moves in the direction A, the crack C in the metallic material M also moves in the direction A. With time the crack C will move under the second receiving coil 9. The crack C has a main direction of extension essentially parallel with the second winding portion 5b and thus the second current $i_2$. Therefore the magnetic field strength is altered less than when passing the first receiver coil 7.

The detected change in the magnetic field strengths is reflected in the voltages induced in the first receiver coil 7 and in the second receiver coil 9. As a result, the first signal and the second signal provided by the first amplifying circuit 7-1 and the second amplifying circuit 9-1, respectively, also reflect the change in magnetic field strengths.

The first signal S1 and the second signal S2 are analysed and A/D converted in the signal processing unit 17. Analysis of the first signal S1 and the second signal S2 can for instance involve determining a mean value of each of the first signal S1 and the second signal S2 between specific points in time based on time changes in the time-varying current i(t). In one embodiment, the specific points in time based on time changes in the time-varying current i(t) can be provided by the control signal C2 from the control unit 15.

A/D converted signals of the first signal S1 and the second signal S2 are provided to the computing unit 19. Signal values of the A/D converted signals are in a first step compared with reference values corresponding to a metallic material without cracks and having the same metallic composition as the metallic material M. The comparison can for instance involve determining a difference between the signal value of each A/D converted signal and the reference value.

Based on the comparison of the signal values of the A/D converted signals with the reference values, crack parameters such as crack length, crack direction and crack depth can be determined in the computing unit 19. The crack direction may for instance be determined by determining a relation between the values obtained by determining the differences between the reference value and each of the A/D converted signals.

In embodiments where α is 90 degrees, a crack angle β, i.e. the crack direction, relative the normal of one of the first winding portion 5a and the second winding portion 5b can be determined by means of the relation:

$$B=57.3*\mathrm{arccot}(dS1/dS2),$$

where dS1 is the change of the signal provided by the first receiver coil 7 due to a crack, and dS2 is the change of the signal provided by the second receiver coil 9 due to the crack. It is to be noted that the above relation may be utilised in any of the four examples presented herein when the angle between a first winding portion and a second winding portion is 90 degrees and the first winding portion and the second winding portion are arranged to detect cracks along the same strip.

As the metallic material M moves in the direction A the entire strip S may be inspected for cracks by means of the process described above.

In one embodiment, the coil arrangement 3-1 is so oriented in relation to a metallic material for inspection that the first winding portion 5a and the second winding portion 5b each intersect the direction of movement A of the metallic material M with about 45 degrees. In this embodiment, the same applies for winding 7a of first receiver coil 7 and for winding 9a of the second receiver coil 9.

In one embodiment, the first winding portion is arranged essentially perpendicular to the direction of movement of the metallic material, and the second winding portion is arranged essentially parallel with the direction of movement of the metallic material. Also in this embodiment, the winding of the first receiver coil is arranged essentially parallel with the first winding portion and the winding of the second receiver coil is arranged essentially parallel with the second winding portion.

A second example of an arrangement for detecting cracks will now be described with reference to FIGS. 2a-b. The second embodiment is especially suitable for detecting cracks which are essentially perpendicular to or parallel with the direction of movement of a metallic material being inspected for cracks.

Figure 2A:
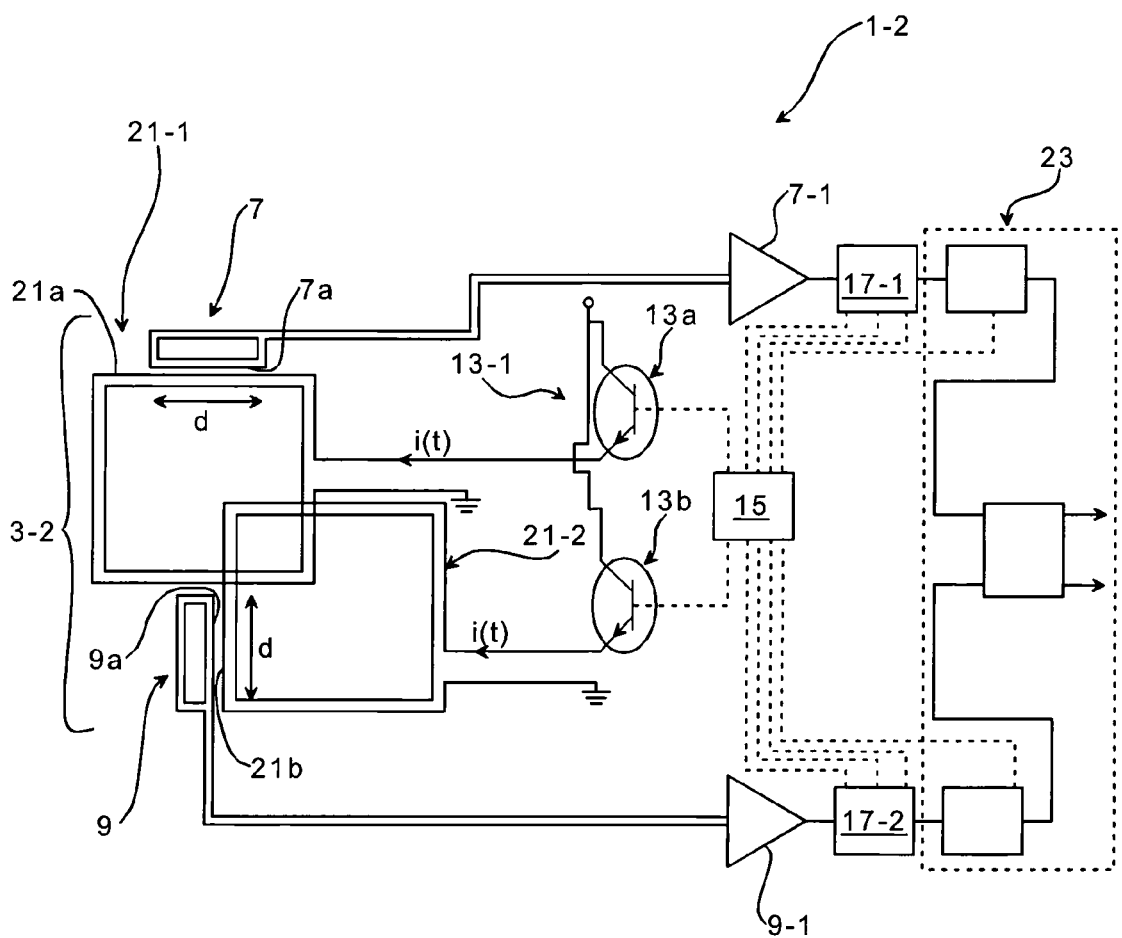
FIG. 2A is a schematic top view of a second example of an arrangement for crack detection in a metallic material.
Figure 2B:
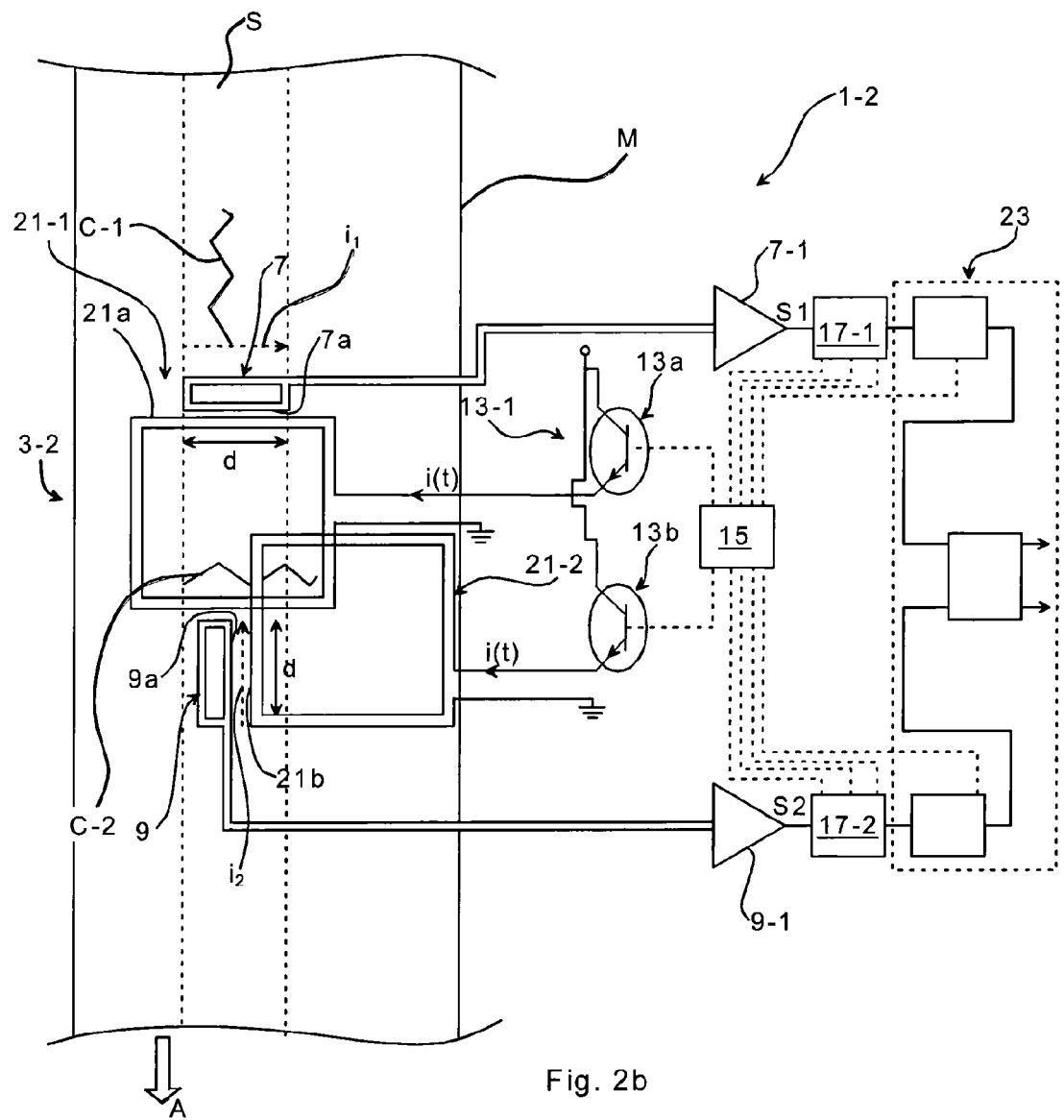

FIG. 2a shows a schematic view of an arrangement 1-2 for crack detection along a strip in a moving metallic material. Arrangement 1-2 comprises a coil arrangement 3-2, a first amplifying circuit 7-1, a second amplifying circuit 9-1, a signal generator 13-1 in this example comprising a first transistor 13a and a second transistor 13b, a control unit 15 for controlling the signal generator 13-1, signal processing units 17-1 and 17-2, and a computing unit 23.

The coil arrangement 3-2 comprises a first transmitter coil 21-1 having a first winding portion 21a defining one side of the first transmitter coil 21-1, a second transmitter coil 21-2 having a second winding portion 21b defining one side of the second transmitter coil 21-2, a first receiver coil 7 having a winding portion 7a, and a second receiver coil 9 having a winding portion 9a.

The first transmitter coil 21-1 and the second transmitter coil 21-2 are separate coils. In particular, the first winding portion 21a and the second winding portion 21b are electrically separated in the sense that each of the first winding portions 21a and the second winding portion 21b can be fed with an individual time-varying current. In the example shown in FIG. 2a, each of the first transmitter coil 21-1 and the second transmitter coil 21-2 has an essentially rectangular shape.

The first winding portion 21a and the second winding portion 21b are essentially perpendicular to each other. The first winding portion 21a and the second winding portion 21b are arranged to receive time-varying currents i(t) from the signal generator 13-1 via their respective transistor 13a and 13b. A respective magnetic field is thereby generated in a portion of a strip of a metallic material moving under the coil arrangement 3-2, inducing a first current and a second current, respectively, in the metallic material as will be further elaborated with reference to FIG. 2b further below.

The first receiver coil 7 and the second receiver coil 9 are oriented in such a way relative the first winding portion 21a and the second winding portion 21b, respectively, that they can detect a respective magnetic field generated by the first current and the second current.

In one embodiment winding portion 7a of the first receiver coil 7 may be defined as that winding of the first receiver coil 7 which is essentially parallel with the first winding portion 21a, whereas winding portion 9a of the second receiver coil 9 may be defined as that winding of the second receiver coil 9 which is essentially parallel with the second winding portion 21b. It is to be noted that the first receiver coil 7 and the second receiver coil 9 in the second example are structurally the same as in the first example. Furthermore, it is to be noted that the first receiver coil and the second receiver coil may be arranged in a plurality of orientations relative the first winding portion and the second winding portion as long as they are placed such that they can detect the currents induced in the metallic material for inspection by the first winding portion and the second winding portion, respectively.

The first receiver coil 7 is arranged at a side of the first winding portion 21a. The second receiver coil 9 is arranged at a side of the second winding portion 21b. In particular the first receiver coil 7 and the second receiver coil 9 are both being arranged in the same plane as the first winding portion and the second winding portion, i.e. in a plane parallel with a surface of a metallic material to be inspected for cracks.

The extension of each of the first winding portion 21a and the second winding portion 21b is essentially constant over at least a distance d corresponding to the longitudinal extension of the winding 7a of the first receiver coil 7, and the winding 9a of the second receiver coil 9, respectively.

The arrangement 1-2 will now be described in more detail in operation with reference to FIG. 2b. In FIG. 2b a metallic material M with a first crack C-1 and a second crack C-2 along a strip S to be inspected for cracks is shown together with the arrangement 1-2. In the example of FIG. 2b, the metallic material M has a direction of movement A, which is downwards in the drawing. When the metallic material M is inspected for cracks, it is preferred that the metallic material M moves with a constant speed under the coil arrangement 3-2.

The control unit 15 is arranged to provide control signals to the signal generator 13-1 to thereby control the time-varying currents i(t) provided by the first transistor 13a and the second transistor 13b to the first winding portion 21a and the second winding portion 21b, respectively. The control signals are preferably such that the signal generator 13-1, via the first transistor 13a and the second transistor 13b, alternatingly can provide a time-varying current i(t) to each of the first winding portion 21a and the second winding portion 21b to thereby alternatingly induce a first current $i_1$ and a second current $i_2$ in the metallic material M.

Thus, in a first step of crack inspection of the metallic material M, a time-varying current i(t) in the form of a current pulse is received by the first transmitter coil 21-1 from the first transistor 13a which in the first step is in its open state. The current pulse may have constant amplitude. The current during this first step is preferably constant and the duration of the current pulse is at least long enough to permit the magnetic field thereby created to penetrate to a depth into the metallic material essentially deeper than the depth of the deepest crack to be measured.

In a second step control unit 15 controls the first transistor 13a such that the first transistor 13a closes, wherein no current is provided by the first transistor 13a. The duration of the second step is in one embodiment about the same as the duration of the current pulse applied in the first step. The first current $i_1$ is, in response to the sudden drop of current magnitude, induced in the metallic material M by means of the first winding portion 21a. The first current $i_1$ flows in a direction parallel with the extension of the first winding portion 21a. A magnetic field generated by the first current $i_1$ and detected by the first receiver coil 7 is provided to the first amplifier circuit 7-1.

In a third step a time-varying current i(t) in the form of a current pulse is received by the second transmitter coil 21-2 from the second transistor 13b which in the third step is in its open state. The current pulse may have constant amplitude. In one embodiment all current pulses have essentially the same amplitude. The third step is similar to the first step described above for the first transmitter coil 21-1.

In a fourth step the control unit 15 controls the second transistor 13b such that the second transistor 13b closes, wherein no current is provided by the second transistor 13b. The duration of the second step is the same or essentially the same as the duration of the second step. The second current $i_2$ is, in response to the sudden drop of current magnitude, induced in the metallic material M by means of the second winding portion 21b. The second current $i_2$ flows in a direction parallel with the extension of the second winding portion 21b. A magnetic field generated by the second current $i_2$ and detected by the second receiver coil 9 is provided to the second amplifier circuit 9-1.

The first amplifying circuit 7-1 provides a first signal S1, which is an amplified signal of the detected magnetic field provided by the first receiver coil 7, to the signal processing unit 17-1. The second amplifying circuit 9-1 provides a second signal S2, which is an amplified signal of the detected magnetic field provided by the second receiver coil 9, to the signal processing unit 17-2. The first signal S1 and the second signal S2 can further be processed in the computing unit 23 for comparison with reference values of a metallic material without cracks and for comparison between them in order to determine whether a crack is present in that portion of the strip into which the first current $i_1$ and the second current $i_2$ have been induced. Moreover, the direction of a detected crack is also determined.

The above procedure is repeated as the metallic material M moves relative the arrangement 1-2 to thereby inspect the entire strip S.

Figure 3:
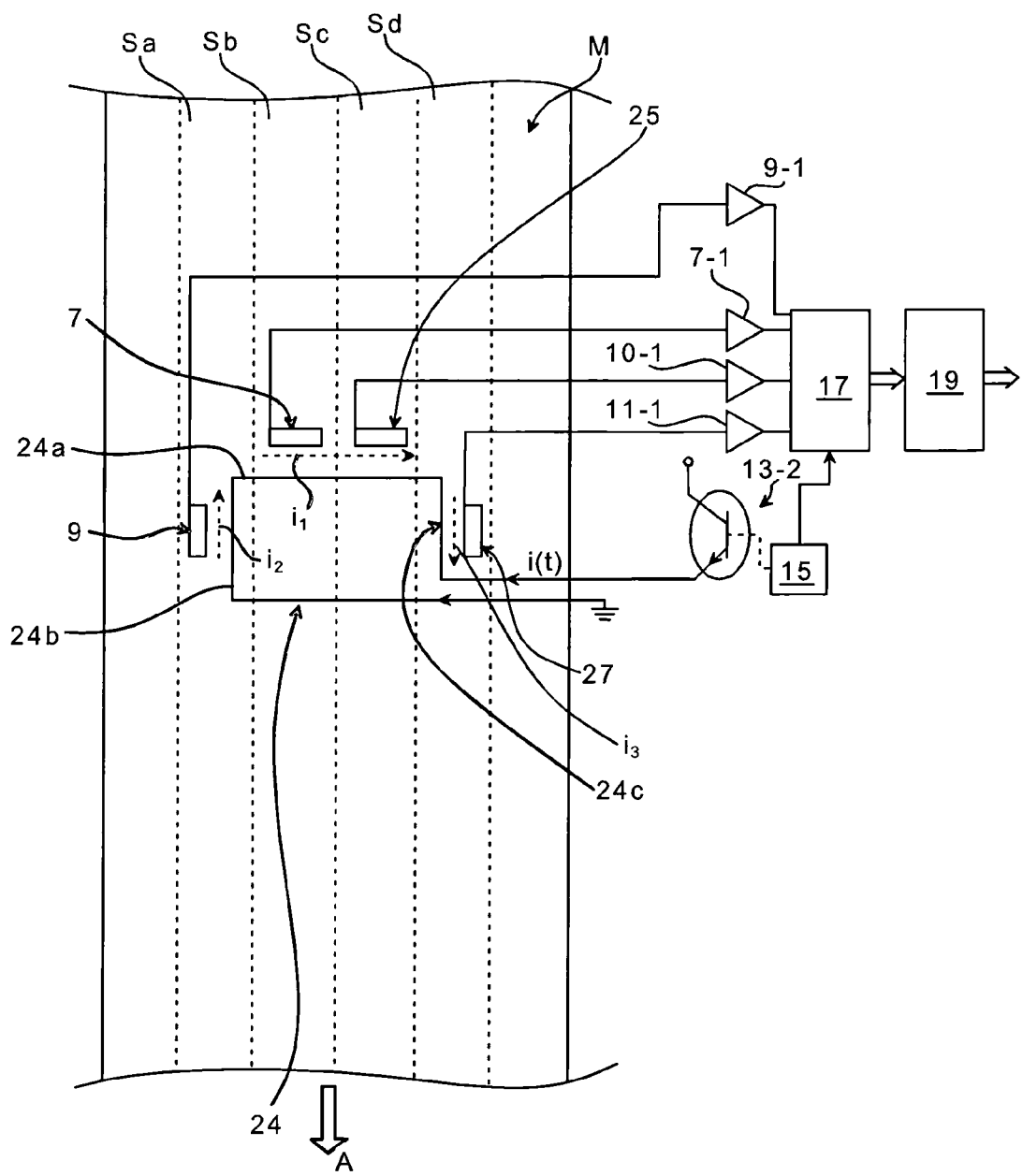
FIG. 3 is schematic view of a third example of an arrangement for crack detection.

FIG. 3a illustrates a third example of an arrangement for detecting cracks in a metallic material M. Arrangement 1-3 is similar to the arrangement 1-2. Coil arrangement 3-3 in the third example however comprises one transmitter coil 24, a first receiver coil 7, a second receiver coil 9, a third receiver coil 25, and a fourth receiver coil 27.

The transmitter coil 24 has a first winding portion 24a arranged adjacent the first receiver coil 7 and the third receiver coil 25, a second winding portion 24b arranged perpendicular or essentially perpendicular with the first winding portion 24a, and a third winding portion 24c arranged perpendicular or essentially perpendicular with the first winding portion 24a and adjacent the fourth receiver coil 27.

The arrangement 1-3 further comprises a signal generator 13-2 for instance in the form of a transistor, a control unit 15, a first amplifying circuit 7-1, a second amplifying circuit 9-1, a third amplifying circuit 10-1, a fourth amplifying circuit 11-1, a signal processing unit 17, and a computing unit 19.

The operation of the third example is similar to the previous examples and will therefore only be described shortly herein.

In operation the signal generator 13-2 is fed with control signals from the control unit 15 in order to control the switching of the signal generator 13-2 which thereby can feed a time-varying current i(t) to the transmitter coil 24, and thus to each of the first winding portion 24a, the second winding portion 24b and the third winding portion 24c. The time-varying current i(t) may for instance be current pulses, as has been described hereabove.

As the time-varying current i(t) flows in the transmitter coil 24 it induces currents, and hence magnetic fields, in different directions in a metallic material M moving in a direction A relative the coil arrangement 3-3. The first winding portion 24a induces a first current $i_1$ in a first direction in the metallic material. The second winding portion 24b induces a second current $i_2$ in the metallic material M, the second current $i_2$ being essentially perpendicular to the first current $i_1$. The third winding portion 24c induces a third current $i_3$ in the metallic material M essentially parallel with the second current $i_2$.

The first receiver coil 7 is arranged to be able to detect a magnetic field created by the first current $i_1$. The second receiver coil 9 is arranged to be able to detect a magnetic field created by the second current $i_2$. The third receiver coil 25 is arranged to be able to detect a magnetic field created by the first current $i_1$ at a different location than the first receiver coil 7. The fourth receiver coil 27 is arranged to be able detect the third current $i_3$.

The second receiver coil 9 is for crack detection along a first strip Sa of the metallic material M. The first receiver coil 7 is for crack detection along a second strip Sb of the metallic material M. The third receiver coil 25 is for crack detection along a third strip Sc of the metallic material M, and the fourth receiver coil 27 is for crack detection along a fourth strip Sd of the metallic material M, the strips Sa-Sd being parallel strips. As elaborated above, the orientation of the first winding portion 24a, the second winding portion 24b and the third winding portion 24c determine the orientation of cracks which can effectively be detected along the strips Sa-Sd.

When the first receiver coil 7, the second receiver coil 9, the third receiver coil 25 and the fourth receiver coil 27 have detected respective magnetic fields by the induction of currents in each of the receiver coils 7, 9, 25, and 27, these signals, i.e. currents, are sent to the amplifying circuits 7-1 to 11-1, respectively, before being received by the signal processing unit 17 and the computing unit 19 for further processing and determination of whether a crack is present in a strip.

Figure 4:
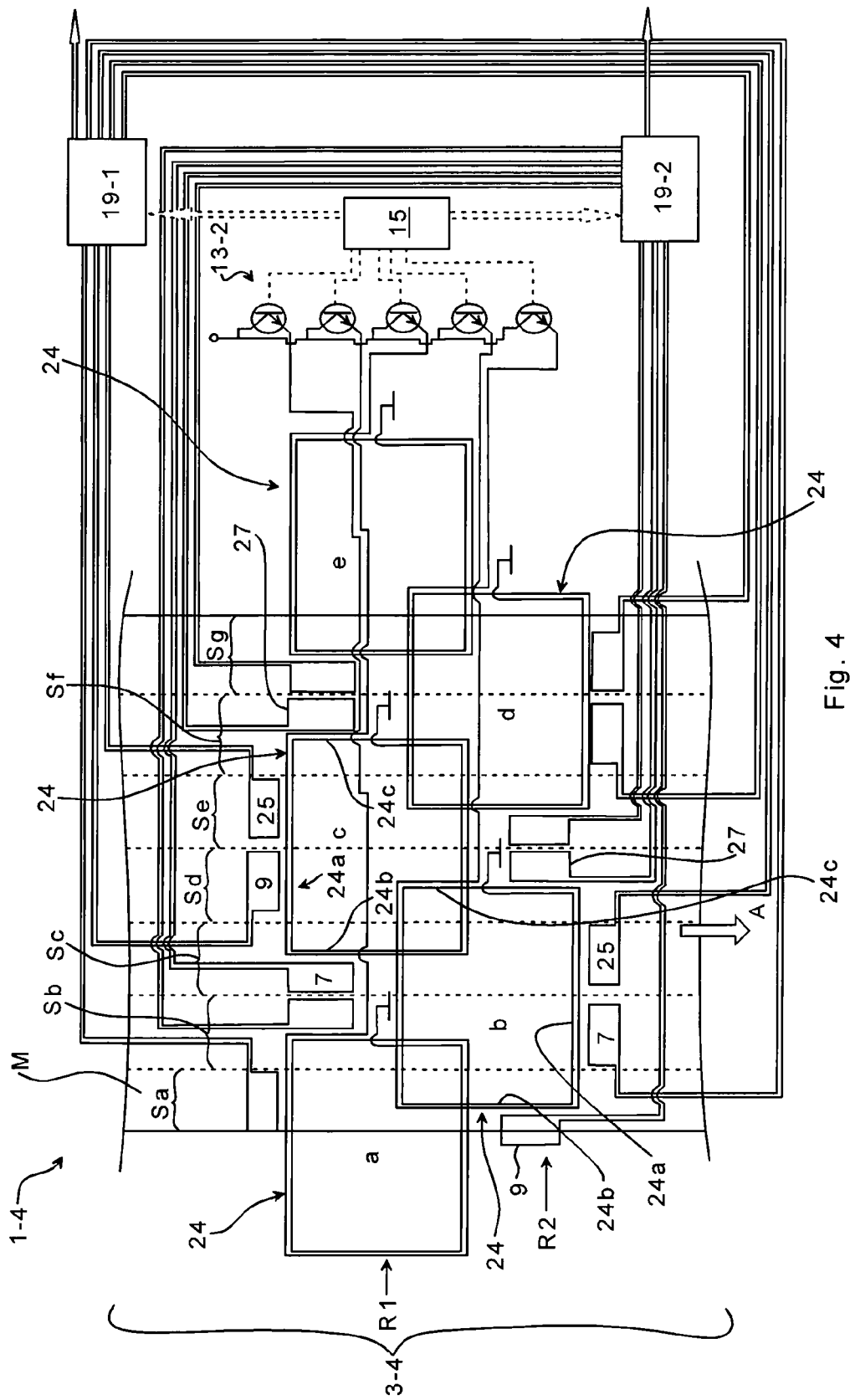
FIG. 4 is a schematic view of a fourth example of an arrangement for crack detection.

FIG. 4 shows a view of a fourth example of an arrangement for detecting cracks in a metallic material M. Arrangement 1-4 comprises a coil arrangement 3-4, a signal generator 13-2 and computing units 19-1 and 19-2.

The arrangement 1-4 may be used for detecting cracks which are parallel with a direction of movement A of the metallic material M relative a coil arrangement 3-4 of the arrangement 1-4, cracks which are essentially perpendicular to the direction of movement A, and also cracks having an orientation between these extremes.

The coil arrangement 3-4 comprises a plurality of transmitter coils 24, arranged in a first row R1 and a second row R2, the transmitter coils 24 in the second row R2 partially overlapping transmitter coils 24 in the first row R1. The transmitter coils 24 of the second row R2 are displaced, in a direction perpendicular to the direction of movement A of the metallic material M relative the coil arrangement 3-4 in relation to the transmitter coils 24 of the first row R1. The second row R2 is downstream relative the first row R1 in the direction of movement A of the metallic material M relative the coil arrangement 3-4. By means of this coil configuration, a scan having a relatively high resolution with respect to cracks may be performed over the entire surface of the metallic material M.

The overlap between the first row R1 and the second row R2 may be arbitrarily selected. In one variation of the fourth example, the transmitter coils of the second row are not displaced relative the first row of transmitter coils.

Each transmitter coil 24 has a first winding portion 24a, a second winding portion 24b and a third winding portion 24c as described above in connection with the disclosure of the third example. Alternatively, isosceles triangle shaped transmitter coils of the type described in the first example may be used to create first and second rows of transmitter coils. Moreover, each transmitter coil 24 which is not arranged to scan a lateral portion of the metallic material M, is associated with four receiver coils placed at sides of the first winding portion 24a, the second winding portion 24b, and the third winding portion 24c as has already been elaborated with reference to the third embodiment.

The transmitter coils 24 in the first row R1 and the second row R2 are fed with time-varying currents i(t) provided by the signal generator 13-2. The signal generator 13-2 may for instance be implemented by means of a chain of transistors. Each transmitter coil 24 may be fed with the time-varying current i(t) via a respective transistor. The switching of the signal generator 13-2 can be controlled by means of the control unit 15.

In one embodiment, the time-varying current i(t) is a current pulse train. The signal generator 13-2 is preferably switched such that only one transmitter coil 24 at a time receives a current pulse from the signal generator 13-2. The transmitter coils 24 may be fed with a current pulse in succession, wherein the magnetic fields generated by a transmitter coil 24 can be detected by its associated receiver coils before another transmitter coil 24 is fed with a current pulse. In one embodiment the current pulses are fed to the transmitter coils 24 in the following order: a, b, c, d, e, where a, b, c, d and e indicate an order of arrangement of the transmitter coils 24. The sequence is thereafter repeated. Each transmitter coil may in one embodiment be activated for about 20 milliseconds, wherein the measurements associated with that transmitter coil are carried out for about 0.1 milliseconds after deactivation of the transmitter coil.

In one variation every other transmitter coil 24 may be activated in each measurement sequence. In a first sequence transmitter coils 24 at positions a, c and e may for instance be activated, wherein in the next sequence transmitter coils 24 at positions b and d may be activated. These sequences are repeated as the metallic material moves in the direction A relative the coil arrangement 3-4. This may be beneficial if a sequence is to be carried out more quickly than would be possible by successively activating all transmitter coils in every iteration of the sequence.

As has been explained above, measurements are typically carried out by receiver coils after a current pulse, e.g. when the current amplitude has been set to essentially zero. Measurements by means of the receiver coils associated with that transmitter coil 24 are typically made before the next current pulse is provided to another transmitter coil 24. This procedure is the same as described above with respect to the third example.

All signals detected by the receiver coils arranged to detect a respective first current are sent to the computing unit 19-1 for processing. All signals detected by the receiver coils arranged to detect a respective second current or third current are sent to the computing unit 19-2 for processing. Cracks having different orientation can thereby be evaluated and detected.

Figure 5:
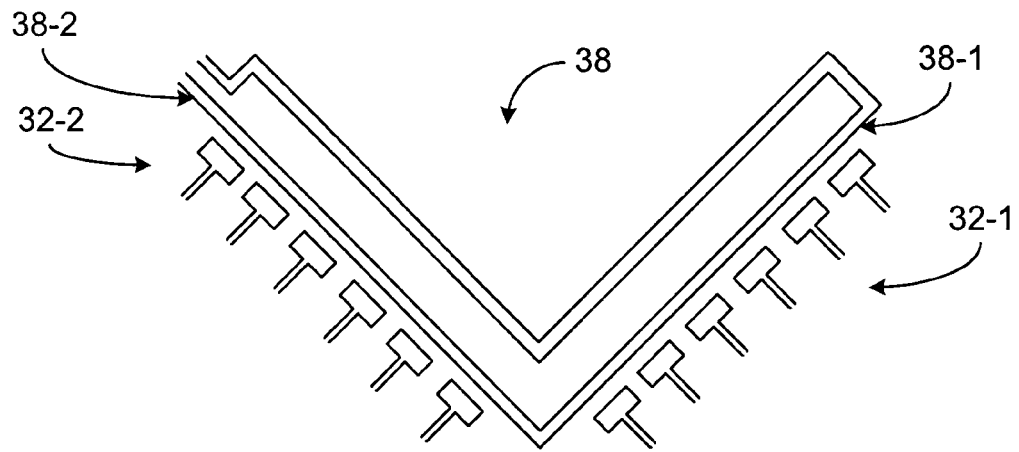
FIG. 5 is a top view of a coil arrangement according to the prior art.

By means of the fourth example, measurements may be carried out along the entire width of the metallic material that is to be inspected for cracks. This is highly advantageous in a metal making process with a moving metallic material where crack detection is made with a fixed coil arrangement 3-4. Advantageously, crack detection may not only be made along the entire width of the metallic material, but the possibility to detect cracks is obtained for any crack orientation. Prior art solutions, such as the arrangement illustrated in FIG. 5, which are not intended for crack detection of metallic materials in metal making, could use one very large transmitter coil for scanning the entire width of a metallic material, with receiver coils being placed along the perpendicular sides of the large transmitter coil. This would however not be suitable for measurements of objects exhibiting high electric resistivity, such as metallic material in a metal making process. Such a large transmitter coil would be too slow for measurements. In order to be able to induce a sufficiently large current in the metallic material that is to be inspected, at a distance of for example 20 mm, on a transmitter coil adequately designed for this measurement problem, giving an inductance of about 0.5-1.0 mH. This would result in a time constant of more than 10-20 µs, which is a time constant that is too slow for measurement of highly electrically resistive objects. In contrast, the arrangement according to the fourth example provided herein, the same induced current could be provided at an inductance of about 0.04 mH, with a time constant of about 1 µs for high electrical resistivity measurements.

Furthermore, it would be difficult to adapt the above-discussed large transmitter coil to a metal making process, because the large coil would have too large internal resistance. For example, if the metallic material has a width of 1.5 m, and the large transmitter coil has 10 winding turns, the total length of the coil would be 60 m. In order to be able to conduct measurements of objects with high electrically resistivity, the circuit wire must be thin, so that no disturbing currents/interference currents are induced in the circuit wire. A suitable wire diameter is 0.05 mm, resulting in a 1 Ω/m resistivity. For a 60 m winding, the resistivity would thus be 60Ω. If the current fed to the transmitter coil for example is 1 A, which is a suitable current for measurements of metallic materials in metal making, the feeding voltage would have to be 60 V, which cannot be considered a low voltage in these applications, and would be a clear disadvantage.

According to one variation, which may apply to any example disclosed herein, each transmitter coil has a smallest dimension, in a plane parallel to a surface of a metallic material to be inspected for cracks when the surface is being inspected for cracks, which is considerably greater than a distance from each of the first winding portion and the second winding portion to the surface when it is inspected for cracks. With the dimension being considerably greater is generally meant that it is at least twice as large as the distance from each of the first winding portion and the second winding portion to the surface. The distance could according to one variation be at least three times as large or at least four times as large, or even more. The distance between each of the first winding portion and the second winding portion and the surface may for example be about 10-20 mm during crack inspection, wherein the smallest dimension, in terms of length and width, of a transmitter coil may be in the range of about 30-120 mm, 40-120 mm, 50-120 mm, 60-120 mm or even greater than that. The dimensions discussed in this paragraph apply to any winding portion of any example disclosed herein.

Figure 6A:
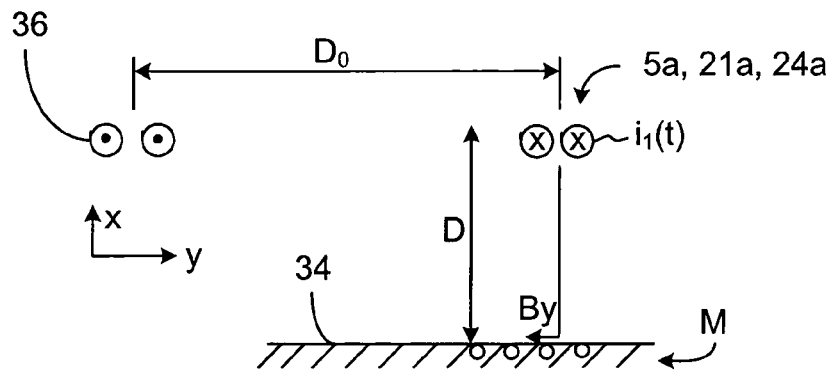
FIGS. 6A-B show schematic cross-sectional side views of a transmitter coil according to the present disclosure and the prior art, respectively.

FIG. 6a depicts a cross-sectional side view of a first winding portion 5a, 21a, 24a according to any example presented herein. It is to be noted that the following description equally applies to any winding portion described herein, e.g. second winding portions. During crack inspection of a metallic material M in a metal-making process, the first winding portion 5a, 21 a, 24a, as well as the entire transmitter coil of which it forms part, is arranged at a distance D from the surface 34 of the metallic material M. In FIG. 6a, a first current $i_1(t)$ flows through the first winding portion 5a, 21a, 24a. The first current $i_1(t)$ induces a current in the metallic material M, flowing in the opposite direction relative the flow direction of the first current $i_1(t)$ in the first winding portion 5a, 21a, 24a. The distance $D_0$ between the return circuit 36 of the transmitter coil, in which the current flows back to the signal generator, and the first winding portion 5a, 21 a, 24a is not illustrated to scale. The planar dimension, i.e. the length and width dimension, of the transmitter coil is considerably greater than the distance D from the first winding portion 5a, 21a, 24a to the surface 34.

Figure 6B:
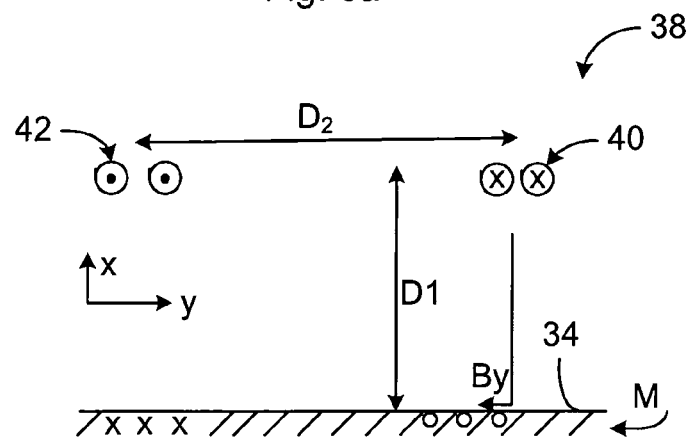

FIG. 6b shows a corresponding example of a prior art transmitter coil 38 which has a transmitter portion 40 and a return circuit portion 42. The transmitter coil 38 and thus the transmitter portion 40 is arranged at a distance $D_1$ from the surface 34 of the metallic material M that is to be inspected for cracks. The transmitter portion 40 and the return circuit portion 42 are arranged at a distance $D_2$ from each other. As can be seen in FIG. 6b, the distances $D_1$ and $D_2$ are essentially the same. Due to the relative proximity of the transmitter portion 40 and the return circuit portion 42, in relation to the distance $D_1$ from the transmitter portion 40 to the surface 34, oppositely directed electromagnetic fields created by the return circuit portion 42 provide a disturbance factor to the total electromagnetic field below the transmitter portion 40.

The advantages with the relative dimensions of the design shown in FIG. 6a compared to that shown in FIG. 6b in a metal making process will now shortly be described. Assuming that the first winding portion 5a, 21 a, 24a of FIG. 6a and the transmitter portion 40 of FIG. 6b are fed with a current of the same magnitude, and that they have the same number of windings, the electromagnetic field above the metallic material will be greater in FIG. 6a. As a result, also the current induced in the metallic material M becomes greater. Therefore, also the current induced in the associated receiver coil will become greater, and thus the detection of cracks becomes more sensitive. In FIG. 6a, the magnetic field $B_y$ in parallel with the metallic material M below the first winding portion 5a, 21a, 24a is determined by the relation $B_y$=Constant/D, whereas the same magnetic field below the transmitter portion 40 of the transmitter coil 38 in FIG. 6b is determined by the relation $B_y$=Constant/$D_1$−Constant*$D_1$/($D_2^2$+$D_1^2$). The current induced in the metallic material M in both cases is proportional to the magnetic field $B_y$. From these relations, it can further be concluded that the design in FIG. 6b is more sensitive to distance variation between the surface 34 of the metallic material M and the transmitter coil 38. In contrast, by means of the design depicted in FIG. 6a, it is substantially easier to conclude whether a current variation in a receiver coil is due to a distance variation between the transmitter coil and the surface 34 or if the current variation is due to a crack in the surface 34. This is particularly relevant when the coil arrangement is fixedly arranged during crack detection, wherein the distance from the surface 34 to the transmitter coil may vary considerably. Finally, the greater dimension of the transmitter coil according to the present disclosure results in that a wider area may be scanned by a transmitter coil, since the currents will be induced in a wider area in the y-direction, as shown in FIG. 6a.

Furthermore, according to any example disclosed herein each of the first winding portion and the second winding portion may have a straight extension in a plane parallel to the surface that is to be inspected for cracks during crack inspection, or at least an extension of such a shape that they induce currents flowing in a straight direction in a metallic material that is being inspected for cracks. A distance from the first winding portion to the first receiver coil is essentially the same as a distance from the first winding portion to a surface of a metallic material to be inspected for cracks when the surface is being inspected for cracks. A distance from the second winding portion to the second receiver coil is essentially the same as a distance from the second winding portion to a surface of a metallic material to be inspected for cracks when the surface is being inspected for cracks. Thus the distance from each of the first winding and the second winding to the surface of the metallic material during inspection is of the same order of magnitude as the distance between a winding portion and its associated receiver coil. As an example a first distance from the first winding portion to the first receiver coil may differ less than 40%, according to one embodiment even less than 20%, from a second distance from the first winding portion to the surface of a metallic material to be inspected for cracks when the metallic material is in position for crack inspection. According to one embodiment the difference in length between the first distance and the second distance may be less than 10%. These relations between the corresponding distances apply mutatis mutandis to the second winding portion and second receiver coil, as well as any winding portion and associated receiver coil of any example presented herein. Preferably, all winding portions and receiver coils of all examples presented herein have length and width extensions arranged in the same plane, essentially parallel to the surface of a metallic material during crack inspection.

Figure 7A:
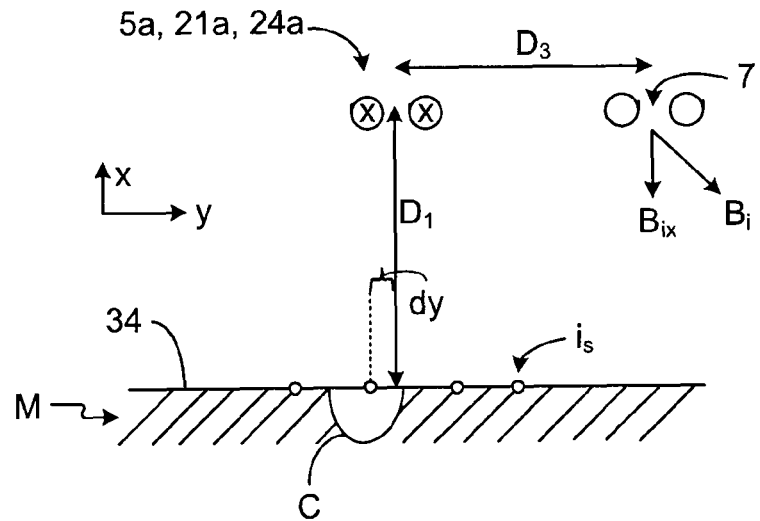
FIGS. 7A-B show schematic cross-sectional side views of a transmitter coil and receiver coil according to the present disclosure and the prior art, respectively.
Figure 7B:
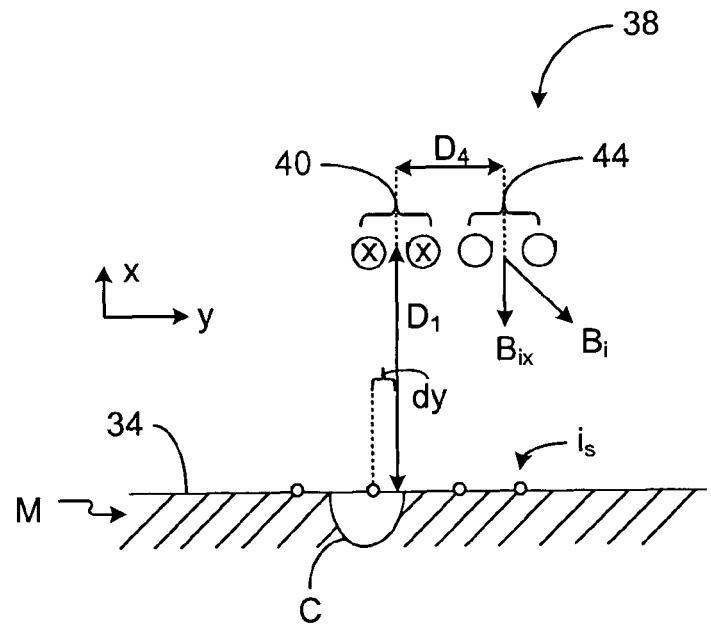

FIGS. 7a and 7b show schematic cross-sectional side views of a transmitter coil and receiver coil according to an example of the present disclosure, and a transmitter coil 38 and associated receiver coil 44 with the dimensions suggested in GB 2 401 947 used in a metal making process, respectively. It is to be noted that the following description equally applies to any winding portion described herein, e.g. first winding portions and second winding portions. During crack inspection of a metallic material M in a metal-making process, the first winding portion 5a, 21 a, 24a, as well as the entire transmitter coil of which it forms part, is arranged at a distance D from the surface 34 of the metallic material M which is in position for crack inspection.

In FIG. 7a, a first current $i_1(t)$ flows through the first winding portion 5a, 21a, 24a. The first current $i_1(t)$ induces a current in the metallic material M, flowing in the opposite direction relative the flow direction of the first current $i_1(t)$ in the first winding portion 5a, 21a, 24a. The associated receiver coil, i.e. the first receiver coil 7 in this case, is arranged at a distance $D_3$ from the first winding portion 5a, 21 a, 24a, the distance $D_3$ being of the same order of magnitude as the distance from the first winding portion 5a, 21a, 24a to a surface 34 of a metallic material M which in position for being inspected for cracks C.

FIG. 7b shows a corresponding example of a prior art transmitter coil 38 which has a transmitter portion 40 and a receiver coil 44. The transmitter coil 38 and thus the transmitter portion 40 is arranged at a distance $D_1$ from the surface 34 of the metallic material M that is to be inspected for cracks. The receiver coil 44 is arranged at a distance $D_4$ from the transmitter coil 38. As can be seen, the distance $D_4$ between the transmitter coil 38 and the receiver coil 44 is considerably less than the distance $D_1$ between the transmitter coil 38 and the surface 34 of the metallic material M that is in position for crack inspection.

Assuming that the first winding portion 5a, 21a, 24a of FIG. 7a and the transmitter portion 40 of FIG. 7b are fed with a current of the same magnitude, and that they have the same number of windings, the electromagnetic field above the metallic material will be greater in FIG. 7a. As a result, also the current induced in the metallic material M becomes greater. Therefore, also the current induced in the associated receiver coil will become greater, and thus the detection of cracks becomes more sensitive. In FIG. 7a, the x-component $B_{ix}$ of the magnetic field $B_i$ created by a current $i_s$ induced in the metallic material M is determined by the relation $$B_{ix}=\text{Constant}*i_s*D_3/(D_3^2+D^2).$$

The corresponding magnetic field $B_{ix}$ in FIG. 7b is determined by the relation $$B_{ix}=\text{Constant}*i_s*D_4/(D_4^2+D_1^2).$$

A crack C in the surface 34 appearing below the first receiver coil 5a, 21 a, 24a in FIG. 7a or below the transmitter coil 40 in FIG. 7b, alters that induced current $i_s$ in the metallic material M which encounters the crack C. Thereby also the magnetic field $B_i$ is altered. The change $dB_{ix}$ in the x-component $B_{ix}$ of the magnetic field can be estimated by the relation $$dB_{ix}=\text{Constant}*i_s(D_3+dy)/((D_3+dy)^2+D^2)$$

for the arrangement in FIG. 7a, while the change $dB_{ix}$ in the x-component $B_{ix}$ of the magnetic field for the arrangement of the prior art in FIG. 7b may be estimated be the relation $$dB_{ix}=\text{Constant}*i_s(D_4+dy)/((D_4+dy)^2+D_1^2)$$

By comparing these relations, it can for example be concluded that, if in FIG. 7a the distance D is equal to D3, and if in the prior art arrangement of FIG. 7b the distance D1 is four times as great as D4, the change in $dB_{ix}$ will be about twice as great in the arrangement of FIG. 7a. Moreover, it can also be concluded that distance variations between the surface 34 and the first winding portion 5a, 21a, 24a affects crack measurements less than is the case for the transmitter coil 38 in FIG. 7b. In the arrangement in FIG. 7a it is therefore considerably easier to determine whether a change in the magnetic field strength is due to a crack or due to a distance variation between the first winding portion 5a, 21 a, 24a and the surface 34.

Moreover, it can also be concluded that the arrangement in FIG. 7a is less sensitive to changes in the magnitude of dy compared to the arrangement in FIG. 7b. Thus, changes in deviation of a crack from the centre line of the first receiver coil 5a, 21 a, 24a along the x-axis creates a relatively small change in the magnetic field B, which can be detected by the receiver coil 7, compared to the arrangement in FIG. 7b. Thereby efficient crack detection along the y-axis may be maintained with fewer receiver coils.

As mentioned earlier, any embodiments presented herein e.g. the fourth example above, may have transmitter coils with dimensions as described hereabove. Moreover, the distance between each transmitter coil and therewith associated receiver coils may be as described above.

In order to maintain the desired distance between the coil arrangement and the surface of the metallic material which is to be inspected, the arrangement according to any example herein may comprise a protection member for example in the form of a flat disk that may be arranged on that surface of the coil arrangement which is arranged to face the metallic material that is to be inspected. Hence, the protection member is sandwiched between the coil arrangement and a metallic material when the arrangement is in use. The protection member is preferably manufactured of material that allows electromagnetic fields generated by the transmitter coils to penetrate the protection member such that currents may be induced in a metallic material that is to be inspected for cracks. The protection member may comprise a water cooling system for cooling the coil arrangement when crack inspection is carried out on hot surfaces. The thickness of the protection member may for example be about 5-10 mm.

In any of the four examples described above, the coil arrangement may be arranged in or on a substrate thereby defining an essentially flat coil arrangement, having a substantially greater length dimension and width dimension than height dimension, which height dimension is in a direction parallel with a normal to the surface of the metallic material to be inspected when arranged below the coil arrangement. It is however to be noted that other designs are also possible within the scope of this disclosure.

The inventive concept has mainly been described above with reference to a few embodiments. However, as is readily appreciated by a person skilled in the art, other embodiments than the ones disclosed above are equally possible within the scope of the invention, as defined by the appended claims. The longitudinal extension of the receiver coils may for instance differ between them. Moreover, the shape of the transmitter coils can be any kind of shape, such as circular or elliptical, as long as the extension of the first winding portion and the second winding portion is essentially constant over a distance corresponding to the length of the corresponding receiver coils. Receiver coils may also have different shapes.

What is claimed is:

1. An arrangement for a metal making process for detecting cracks along a strip of a metallic material moving in relation to the arrangement, the arrangement comprising:
   a coil arrangement which is fixedly arranged in the metal making process during crack inspection, wherein the coil arrangement having:
   a first winding portion extending in a first direction for inducing a first current in the first direction in a portion of the strip,
   a second winding portion extending in a second direction for inducing a second current in the second direction in the portion of the strip, the first direction and the second direction intersecting each other,
   a first receiver coil arranged to detect a magnetic field generated by the first current, and a second receiver coil arranged to detect a magnetic field generated by the second current, the magnetic field generated by the first current and the magnetic field generated by the second current providing a measure of whether a crack is present in the portion of the strip and a direction of the crack,
   wherein the first winding portion is arranged at a first distance from the first receiver coil, said first distance generally parallel to the surface of the metallic material; and
   a protection member arranged to be sandwiched between the coil arrangement and a metallic material when the arrangement is in use, to maintain a second distance between the first winding portion and a surface of the metallic material, wherein the first distance and the second distance differ less than 40%.

2. The arrangement as claimed in claim 1, wherein the first direction and the second direction are essentially perpendicular.

3. The arrangement as claimed in claim 1, wherein the second winding portion is arranged downstream of the first winding portion with respect to a direction of movement of a metallic material during crack inspection thereof.

4. The arrangement as claimed in claim 1, wherein the first receiver coil is arranged at a side of the first winding portion and the second receiver coil is arranged at a side of the second winding portion, the first receiver coil and the second receiver coil both being arranged in the same plane as the first winding portion and the second winding portion.

5. The arrangement as claimed in claim 4, wherein a winding of the first receiver coil is arranged in parallel with the first winding portion and a winding of the second receiver coil is arranged in parallel with the second winding portion.

6. The arrangement as claimed in claim 5, wherein the first winding portion has an essentially constant direction of extension along a distance defining a first winding axis where the first winding axis of the first winding portion is parallel with a first receiver axis of the winding of the first receiver coil that extends along an essentially constant direction, and the second winding portion has an essentially constant direction of extension along a distance defining a second winding axis where the second winding axis of the second winding portion is parallel with a second receiver axis of the winding of the second receiver coil that extends along an essentially constant direction.

7. The arrangement as claimed in claim 1, comprising a signal generator arranged to feed a time-varying current to the first winding portion and the second winding portion for inducing the first current and the second current in the metallic material.

8. The arrangement as claimed in claim 1, wherein the first winding portion defines a first leg of an essentially right angled triangular transmitter coil and the second winding portion defines a second leg of the essentially triangular transmitter coil, the first leg and the second leg being essentially perpendicular legs, the first and second receiver coils located outside of a perimeter of the essentially right angled triangular transmitter coil.

9. The arrangement as claimed in claim 1, wherein the first winding portion and the second winding portion form part of electrically separated coils, each of the first winding portion and the second winding portion being arranged to be fed with an individual time-varying current.

10. The arrangement as claimed in claim 9, wherein each of the first winding portion and the second winding portion form part of a respective rectangular shaped transmitter coil.

11. The arrangement as claimed in claim 7, wherein the time-varying current is a pulse train.

12. The arrangement as claimed in claim 7, comprising a control unit for controlling the signal generator to alternatingly provide the time-varying current to each of the first winding portion and the second winding portion to thereby alternatingly induce the first current and the second current in the metallic material.

13. The arrangement as claimed in claim 1, comprising a computing unit arranged to receive signals based on the magnetic field detected by the first receiver coil and on the magnetic field detected by the second receiver coil for determining whether a crack is present in the strip.

14. The arrangement as claimed in claim 13, wherein the computing unit is arranged to determine a direction of extension of a detected crack based on the magnetic field detected by the first receiver coil and on the magnetic field detected by the second receiver coil.

15. The arrangement as claimed in claim 9, comprising:
a third receiver coil having a winding arranged along the same axis as the first receiver coil, the winding of the third receiver coil being arranged to detect the magnetic field generated by the first current.

16. The arrangement as claimed in claim 15, having a third winding portion parallel with the second winding portion for inducing a third current in the metallic material, and a fourth receiver coil having a winding arranged in parallel with the winding of the second receiver coil, the winding of the fourth receiver coil being arranged to detect a magnetic field generated by the third current in the metallic material.

17. The arrangement as claimed in claim 1, wherein the first winding portion forms part of a transmitter coil, which transmitter coil has a smallest dimension, in a plane parallel to a surface of a metallic material to be inspected for cracks when the surface is being inspected for cracks, which is at least twice as large as the second distance.

18. The arrangement as claimed in claim 17, wherein the smallest dimension of the transmitter coil is at least three times as large as the second distance.

19. The arrangement as claimed in claim 1, wherein the first distance and the second distance differ less than 20%.

20. The arrangement as claimed in claim 1, wherein the second winding portion is arranged at a first distance from the second receiver coil, wherein the protection member maintains a second distance between the second winding portion and a surface of the metallic material, wherein the first distance and the second distance differ less than 40%.

21. The arrangement as claimed in claim 20, wherein the first distance and the second distance differ less than 20%.

22. The arrangement as claimed in claim 20, wherein the second winding portion forms part of a transmitter coil, which transmitter coil has a smallest dimension, in a plane parallel to a surface of a metallic material to be inspected for cracks when the surface is being inspected for cracks, which is at least twice as large as the second distance.

23. The arrangement as claimed in claim 22, wherein the smallest dimension of the transmitter coil is at least three times as large as the second distance.

24. The arrangement as claimed in claim 1, wherein the second distance is in a range of 10-20 mm.

25. The arrangement as claimed in claim 1, wherein an another distance between the second winding portion and the surface of the metallic material is in a range of 10-20 mm.

* * * * *